(12) United States Patent
Munaretto (10) Patent No.: US 10,314,538 B2
(45) Date of Patent: Jun. 11, 2019

(54) BIOMECHANICAL MOTION MEASUREMENT

(71) Applicant: Huami Inc., Mountain View, CA (US)

(72) Inventor: Joseph Munaretto, Mountain View, CA (US)

(73) Assignee: Huami Inc., Mountain View, CA (US)

( * ) Notice: Subject to any disclaimer, the term of this patent is extended or adjusted under 35 U.S.C. 154(b) by 239 days.

(21) Appl. No.: 15/251,407

(22) Filed: Aug. 30, 2016

(65) Prior Publication Data

US 2018/0055417 A1    Mar. 1, 2018

(51) Int. Cl.
| | |
|---|---|
| *A61B 5/00* | (2006.01) |
| *A61B 5/08* | (2006.01) |
| *A61B 5/11* | (2006.01) |
| *A61B 5/113* | (2006.01) |

(52) U.S. Cl.
CPC .......... *A61B 5/6826* (2013.01); *A61B 5/0816* (2013.01); *A61B 5/113* (2013.01); *A61B 5/1121* (2013.01); *A61B 5/4566* (2013.01); *A61B 5/6823* (2013.01); *A61B 5/6829* (2013.01); *A61B 2562/0223* (2013.01)

(58) Field of Classification Search
USPC ....................................................... 600/595
See application file for complete search history.

(56) References Cited

U.S. PATENT DOCUMENTS

| | | | |
|---|---|---|---|
| 4,267,845 A | | 5/1981 | Robertson, Jr. et al. |
| 6,898,548 B2 | | 5/2005 | Flament et al. |
| 8,234,798 B2 | | 8/2012 | DiBenedetto et al. |
| 8,529,475 B2 | | 9/2013 | Bonnet |
| 8,821,305 B2 | | 9/2014 | Cusey et al. |
| 9,186,096 B2 | | 11/2015 | Solinsky |
| 9,220,942 B1 | * | 12/2015 | Serkiz ................ A41D 19/0027 |
| 2004/0122334 A1 | | 6/2004 | Yamashiro |
| 2011/0009766 A1 | * | 1/2011 | McCool ................. A61B 5/091 600/534 |
| 2015/0279231 A1 | * | 10/2015 | Kuo ..................... G09B 19/003 702/19 |
| 2016/0086080 A1 | | 3/2016 | Foong et al. |
| 2016/0242646 A1 | * | 8/2016 | Obma ................. A61B 5/0024 |
| 2017/0143494 A1 | * | 5/2017 | Mahfouz ................ A61B 34/20 |
| 2017/0211997 A1 | * | 7/2017 | Kulach ................... G01L 3/247 |
| 2017/0347965 A1 | * | 12/2017 | Elhawary ............... G16H 20/30 |

* cited by examiner

*Primary Examiner* — Daniel L Cerioni
(74) *Attorney, Agent, or Firm* — Young Basile Hanlon & MacFarlane, P.C.

(57) ABSTRACT

A method for measuring body movement with a wearable device. The method includes receiving, from a magnetic sensor of the wearable device, first signal data indicative of a magnetic field of a wearable magnet, wherein the wearable device is placed on a first body segment and the wearable magnet is placed on a second body segment; determining, by a computing device based on the first signal data, a distance metric indicative of a relative distance between the wearable magnet and the wearable device, and an orientation metric indicative of an orientation relative to the wearable magnet; and determining a biomechanical model based on the type of body segment for the first body segment and the second body segment, wherein the biomechanical model includes a relationship constraint between the distance metric and the orientation metric.

19 Claims, 8 Drawing Sheets

BIOMECHANICAL MOTION MEASUREMENT

BACKGROUND

As ubiquitous computing technology interweaves into daily life, wearable smart devices, such as wristbands, watches, headsets, and glasses, are becoming more and more popular. These wearable smart devices attempt to measure the physiological state of the user, and some of these devices focus on measurements made in order to estimate the wearer's body position. The position and orientation of the various parts of the human body can be difficult to infer from sensors positioned at a single location, or based on estimated orientations relative to the earth's magnetic field. Soft magnetic materials contained in wearable items can interfere with readings made relative to the earth's magnetic field.

SUMMARY

Disclosed herein are aspects of systems, methods, and apparatuses for measurement of biomechanical motion using magnetic sensors.

One aspect of the disclosure is a method for measuring body movement with a wearable device. The method includes receiving, from a magnetic sensor of the wearable device, first signal data indicative of a magnetic field of a wearable magnet, wherein the wearable device is placed on a first body segment and the wearable magnet is placed on a second body segment; determining, by a computing device based on the first signal data, a distance metric indicative of a relative distance between the wearable magnet and the wearable device, and an orientation metric indicative of an orientation relative to the wearable magnet; and determining a biomechanical model based on the type of body segment for the first body segment and the second body segment, wherein the biomechanical model includes a relationship constraint between the distance metric and the orientation metric.

Another aspect of the disclosure is an apparatus that includes a wearable magnet removably attachable to an accessory component configured to be attached to a first body segment. A wearable device configured to be attached to a second body segment includes a magnetic sensor for detecting a magnetic field intensity of the wearable magnet, and a computing device configured to: receive, from the magnetic sensor, first signal data indicative of a magnetic field of the wearable magnet; determine a distance metric indicative of a relative distance between the wearable magnet and the wearable device, and an orientation metric indicative of an orientation of the wearable magnet; and determine a biomechanical model based on the type of body segment for the first body segment and the second body segment, wherein the biomechanical model includes a relationship constraint between the distance metric and the orientation metric.

Another aspect of the disclosure is an apparatus that includes a wearable magnet removably attachable to an accessory component configured to be attached to a first body segment. A wearable device configured to be attached to a second body segment comprises a first magnetic sensor for detecting a first magnetic field intensity of the wearable magnet, and a computing device configured to be attached to a third body segment. The computing device comprises a second magnetic sensor for detecting a second magnetic field intensity of the wearable magnet, and is configured to: receive, from the first magnetic sensor, first signal data indicative of a magnetic field of a wearable magnet; determine a distance metric indicative of a first relative distance between the wearable magnet and the first magnetic sensor and a second relative distance between the wearable magnet and the second magnetic sensor, and an orientation metric indicative of an orientation of the wearable magnet; determine a biomechanical model based on the type of body segment for the first body segment, the second body segment, and the third body segment, wherein the biomechanical model includes a relationship constraint between the distance metric and the orientation metric; and generate biomechanical output data indicative of a relative posture for the first body segment, the second body segment, and the third body segment based on the biomechanical model These and other aspects of the present disclosure are disclosed in the following detailed description of the embodiments, the appended claims, and the accompanying figures.

BRIEF DESCRIPTION OF THE DRAWINGS

The description herein makes reference to the accompanying drawings, wherein like reference numerals refer to like parts throughout the several views.

DETAILED DESCRIPTION

This disclosure relates to systems, apparatuses, and methods for estimating biomechanical motion using a sensor of a wearable device and a wearable magnet. In an implementation, a sensor, such as a magnetometer, and a magnet are placed on body segments of a user where relative motion is expected. Examples of measurable body segment motion include, but are not limited to, spinal, ankle, and scapular protraction. Respiratory rate may also be measured. Based on signal measurements, such as magnetic field intensities, the relative angle and the relative distance of body segments associated with a user's body motion can be determined according to a biomechanical model. The biomechanical model may be predetermined and/or developed by a learning process of iterative measurements. Biomechanical output may be used to detect and classify unwanted and/or excessive body movements and to send notifications to the user of such detections.

Figure 1:
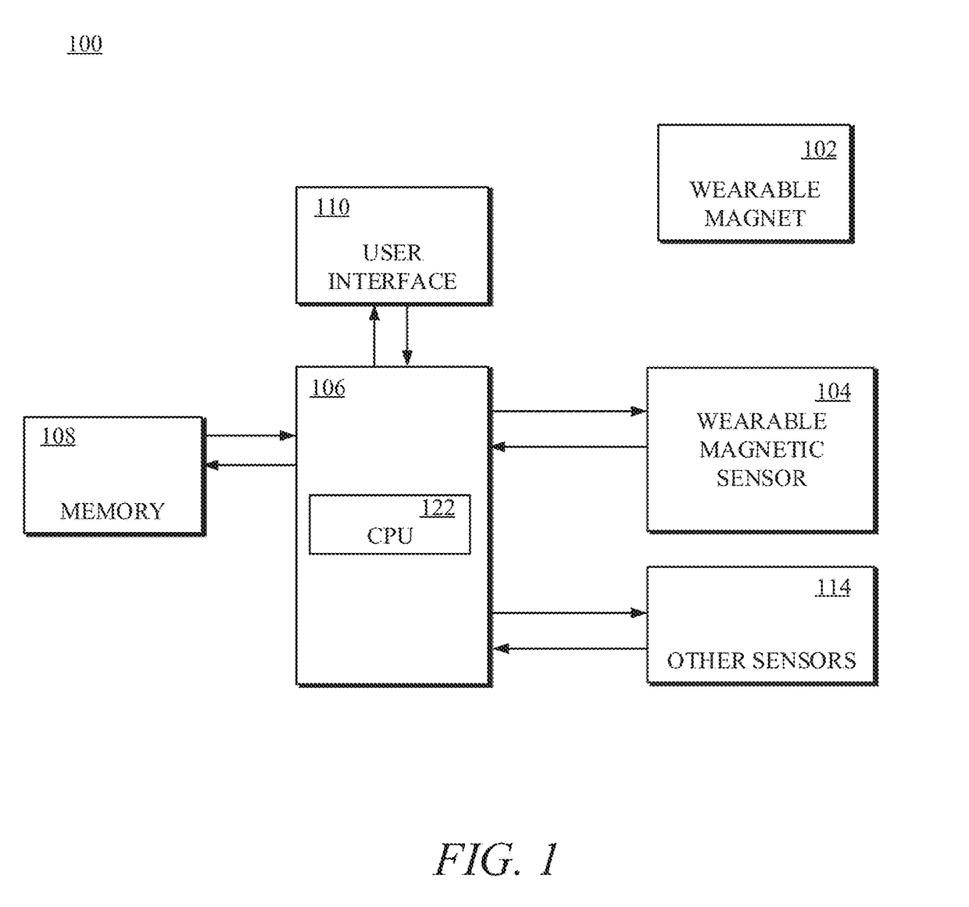
FIG. 1 is a block diagram of an example of an apparatus for measurement of biomechanical motion in accordance with implementations of the present disclosure.

FIG. 1 is a block diagram of an example of a biomechanical measurement device in accordance with this disclosure. Apparatus 100 may function as a biomechanical device and may include a wearable magnet 102, a wearable magnetic sensor 104, a microcontroller 106, a memory unit 108, a user interface 110, other sensors 114, or a combination thereof.

In some implementations, the wearable magnet 102 may be a permanent magnet removably attachable to an accessory component configured to be attached to a body segment where relative motion is to be measured. For example, a permanent magnet may be encapsulated within a case, pocket, or pouch that has means for attachment to an article of clothing, such as a clip, strap, or other form of fastener. In some implementations, the wearable magnet 102 may be removably attachable to an accessory component that has means for affixing directly on a body segment. For example, a strap accessory component may contain the wearable magnet 102 and may be wrapped around a body segment for which motion is to be measured. In some implementations, the wearable magnet 102 may include soft magnetic materials. For example, the wearable magnet 102 may be implemented in an eyeglass frame or a phone.

In some implementations, the wearable magnetic sensor 104 may include a magnetometer, such as, for example, a single axis or three-axis magnetometer. The wearable magnetic sensor 104 can be included in a wearable device such as a smart watch, a fitness tracking wristband, a smart module that can be inserted into a wearable housing, or a smartphone. A three-axis magnetometer in the wearable magnetic sensor 104 may measure an intensity with respect to each of the three axes relative to the distance from the wearable magnet 102. The measured magnetic intensity may also be relative to the orientation angle between the wearable magnet 102 and the magnetometer.

In some implementations, the apparatus 100 may include a plurality of wearable magnetic sensors 104. For example, a first wearable magnetic sensor 104 may be included in a wearable device, such as a smartphone, and one or more wearable magnetic sensors 104 may be removably attachable to an accessory component configured to be attached to a body segment in a location different from that of the first wearable magnetic sensor 104. The plurality of wearable magnetic sensors 104 may be attached to different body segments, or to a common body segment but at different locations thereon such that magnetic field intensity measurements can be obtained from different relative distances and different relative orientation angles with respect to the wearable magnet 102.

Microcontroller 106 may include a central processing unit (CPU) 122, such as a microprocessor, and may include single or multiple processors, each having single or multiple processing cores. Alternatively, microcontroller 106 may include another type of device (or multiple devices), now existing or hereafter developed, capable of manipulating or processing information. When multiple processing devices are present, they may be interconnected in any manner, including hardwired or networked, including wirelessly networked. Thus, the operations of microcontroller 106 may be distributed across multiple machines that can be coupled directly or across a local area or other network. The microcontroller 106 may be a general-purpose processor or a special-purpose processor.

Memory unit 108 may store various modules that may be executed to perform the biomechanical measurements as described herein. Memory unit 108 is shown coupled to microcontroller 106, which may execute the various modules. When the modules are executed, a set of algorithms, processes, or operations may be run for realizing the functions of biomechanical metrics determination, biomechanical model determination, and biomechanical output generation in accordance with this disclosure. Memory unit 108 may be implemented as Random Access Memory (RAM), or may be implemented as any suitable non-permanent storage device that is used as memory. Memory unit 108 can include executable instructions and data for immediate access by CPU 122. Memory unit 108 may include one or more DRAM modules such as, for example, DDR SDRAM. Memory unit 108 may include another type of device (or multiple devices), now existing or hereafter developed, capable of storing data for processing by CPU 122. CPU 122 may utilize a cache as a form of localized fast memory for operating on data and instructions.

User interface 110 may include a screen driver and a display screen used for displaying notifications, allowing a user to view indications of biomechanical motion measurements, such as those exceeding established thresholds. User interface 110 may include an audio device, such as a speaker, that can send audio notifications associated with the biomechanical output. User interface 110 may include means for inputting information associated with the biomechanical measurements, including but not limited to a microphone for voice input, a touchscreen, a keypad, an input/output port for coupling to an auxiliary device for data entry, or a combination thereof. Input information may include distance and/or orientation related data corresponding to the placement of the wearable magnet 102 and the wearable magnetic sensor 104. For example, a motion measurement of a joint between two body segments may include placement of the wearable magnet 102 on the first body segment at a first distance from the joint and placement of the wearable magnetic sensor 104 at a second distance from the joint. In some implementations, using the user interface 110, the values of the first distance and the second distance may be entered by the user as biomechanical metrics input for the apparatus 100, from which a relative motion estimation may be computed.

In some implementations, placement of the wearable magnet 102 and wearable magnetic sensors 104 may be according to predetermined distances. For example, the wearable magnet 102 and one or more wearable magnetic sensors 104 may be arranged as an assembly, physically connected by a flexible coupling to control the relative distance around the body joint, thereby having known distance metrics for the apparatus 100. As another example, the wearable magnet 102 and wearable magnetic sensor 104 may not be physically connected, and placement onto body segments may be user controlled according to instructions provided to the user that correspond with predetermined distance metrics.

In some implementations, one or more other sensors 114 may also be used for estimating relative body segment motion. For example, one or more other sensors 114 can be located at a body segment different from the location of the wearable magnetic sensor 104. The other sensors 114 may include, for example, a nine-axis inertial measurement unit (IMU), a barometric pressure sensor, an electromyography (EMG) sensor, or any other sensor that can be used for estimating relative body motion, including rotational information relative to a body segment.

Figure 2:
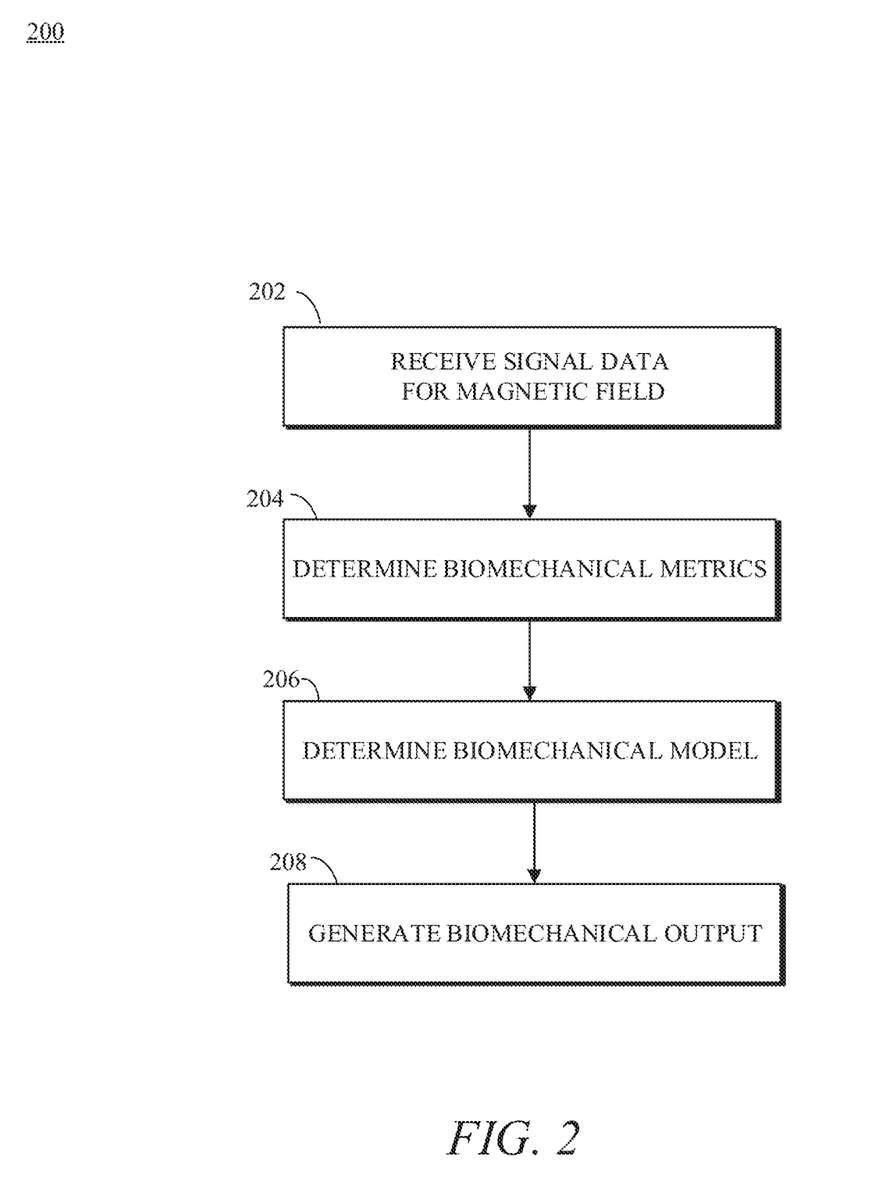
FIG. 2 illustrates an example of a method for measurement of biomechanical motion in accordance with implementations of the present disclosure.

FIG. 2 illustrates an example of a method for measurement of biomechanical motion in accordance with implementations of the present disclosure. In an aspect, biomechanical motion measurement may include receiving signal data for a magnetic field at operation 202, determining biomechanical metrics at operation 204, determining a biomechanical model at operation 206, generating a biomechanical output at operation 208, or a combination thereof.

In some implementations, at operation 202, signal data indicative of a magnetic field of a wearable magnet may be received from a magnetic sensor of a wearable device. For example, a computing device, such as microcontroller 106, may receive signal data from a magnetic sensor, such as wearable magnetic sensor 104, with information associated with a measured magnetic field intensity of a magnet, such as wearable magnet 102. In an aspect, wearable magnet 102 may be attached to a first body segment, wearable magnetic sensor 104 may be attached to a second body segment, and the computing device may be co-located with the wearable magnetic sensor 104 for analyzing the received signal data.

In some implementations, biomechanical metrics, such as a distance metric and/or an orientation metric associated with a relative distance between a wearable magnet and a wearable magnetic sensor, may be determined at operation 204. For example, correspondence between changes in magnetic field intensity to distance metrics and orientation metrics may be retrieved from the memory unit, such as CPU 122 retrieving the metrics from memory unit 108. Correspondence can include, for example, one or more of correlational, functional, or association (or associative) relationships between the metrics. In some implementations, the initial metrics may be determined based on user input, calibration data, or by a physical configuration of apparatus 100 that connects the wearable magnet 102 and the magnetic sensor 104 according to predetermined distance and orientation metrics, or a combination thereof.

In some implementations, a biomechanical model may be determined at operation 206. For example, the pairing of the wearable magnet 102 and wearable magnetic sensor 104 may have particular properties associated with a particular biomechanical configuration (e.g., spinal segments, ankle, wrist, or other body segment joint), which may be defined by a function of intensity and distance across various angles and/or a function of intensity and relative angle across various distances. In some implementations, the biomechanical model may be based on a planar function. For example, a measurement of signal intensity I may be a function of the relative distance and angular relationship between the magnet 102 and the magnetic sensor 104.

In some implementations, the biomechanical model may be a function based on the law of cosines. For example, the estimated angle at the body joint being measured may correspond to changes in the detected magnetic field intensity, which can be represented as a cosine function corresponding to the relative distance of the body segments.

Improvements may be made to the initial biomechanical model by machine learning. For example, an initial model may include a measurable range with limits on the expected body segment motion. After repeated measurements over time, patterns or trends may be detected, and the measurable range may be adjusted accordingly. As such, the biomechanical model may be adapted with respect to limitation to degrees of freedom (such as with respect to body movement).

In some implementations, the biomechanical output may be generated at operation 208. For example, measurement data received from the sensors may be processed to convert into a norm, such as a magnetic field signal intensity, and orientations, such as spherical coordinates that may include relative distance and relative angle. In some implementations, measurement of an isotropic magnetic field may yield a biomechanical output including the relative distance between the magnet 102 and the magnetic sensor 104. Signal processing may include Kalman filtering of multiple signal data received from multiple sensors to determine an absolute orientation of a body segment. For instance, a Bayesian filtering can be used to fuse one or more metrics from one or more sensors such as magnetometer, barometric pressure, accelerometer, and gyroscope sensors, which can be used to statistically constrain what body segment orientations are feasible, and/or to enhance estimation accuracy. Some sensors, such as a barometric pressure sensor, can improve estimation of vertical displacement, while others, such as an accelerometer, can leverage the biomechanical model to identify whether the user is operating at the end of range of motion of a joint.

Figure 3:
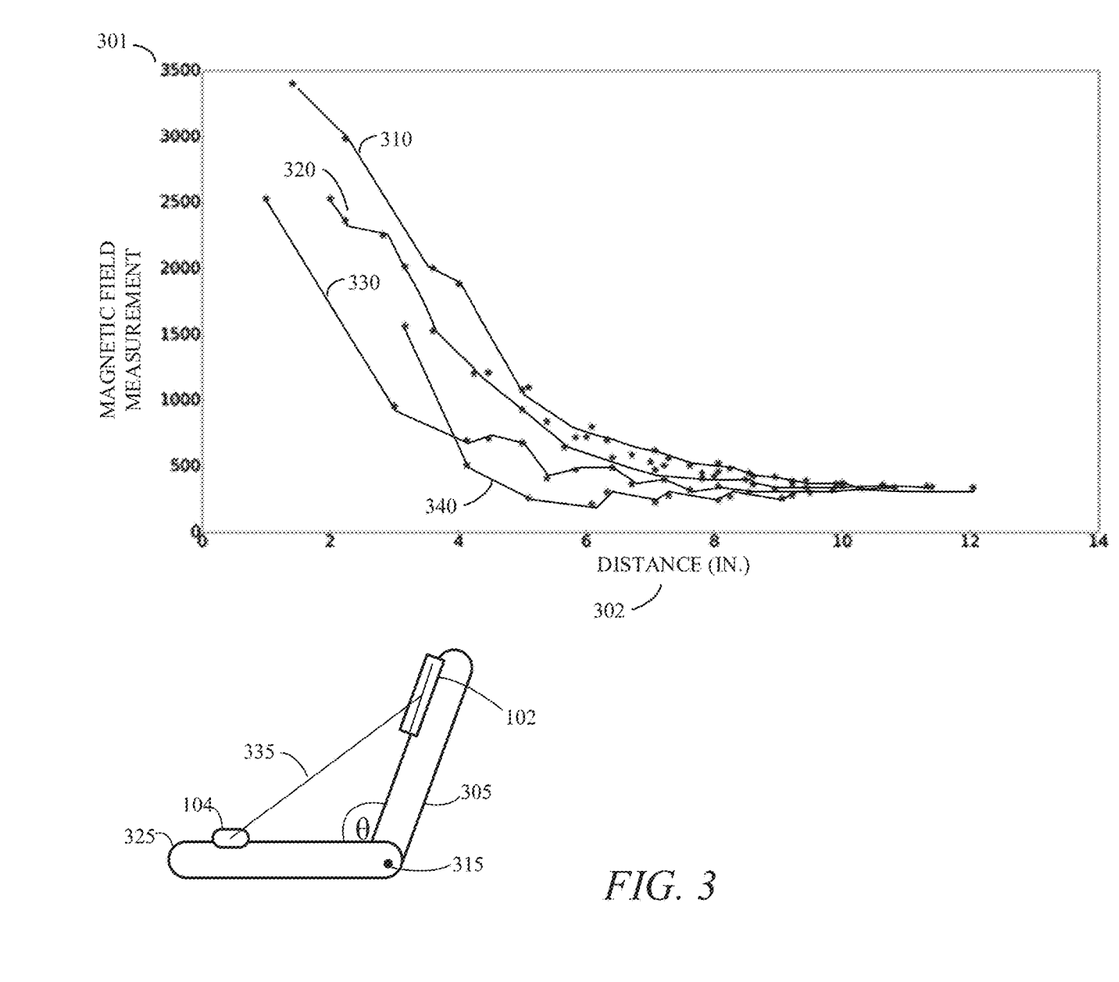
FIG. 3 illustrates an example of biomechanical measurement device characteristics for various sensor orientations in accordance with implementations of the present disclosure.

FIG. 3 illustrates an example of biomechanical measurement device characteristics for various relative orientation angles in accordance with implementations of the present disclosure. In some implementations, characteristic curves 310/320/330/340 for a biomechanical measurement device, such as apparatus 100 of FIG. 1, may be generated based on correspondence between magnetic field intensity measurements 301 and relative distances 302 between the magnet and the magnetic sensor. For example, magnet 102 may be attached to a body segment 305 and magnetic sensor 104 may be attached to body segment 325, having a relative distance 335 between them with respect to a body segment joint 315. The biomechanical measurement characteristics 310/320/330/340 may be generated by performing a series of measurements of, respectively, magnetic field intensity and relative distances, between the magnet 102 and the magnetic sensor 104 at different relative orientation angles $\theta$ between the magnet 102 and the magnetic sensor 104. For example, the wearable magnet 102 may be placed on body segment 305 at a first relative orientation angle $\theta$, and by measuring at varying relative distances 335, the correspondence curve 310 may be generated. Similarly, another correspondence curve 320/330/340 may be generated for correspondence of measured magnetic field intensity 301 to relative distance 302 for a different relative orientations angle $\theta$. In the example of FIG. 3, the magnetic units of measurement can be shown as microTesla ($\mu$T). Other units of measurement can also be used.

The biomechanical measurement characteristic curves 310/320/330/340 may be stored in memory unit 108 for reference by the microcontroller 106 when generating biomechanical motion outputs by mapping received measurements of magnetic field intensity to a corresponding relative distance 302 for the associated orientation angle $\theta$. In some implementations, biomechanical measurement characteristic curves 310/320/330/340 may provide an optimization for biomechanical outputs by defining the relationship of magnetic field intensity input and relative distance/orientation output. A detailed example of the optimization will be set forth in the description of FIG. 5.

Figure 4:
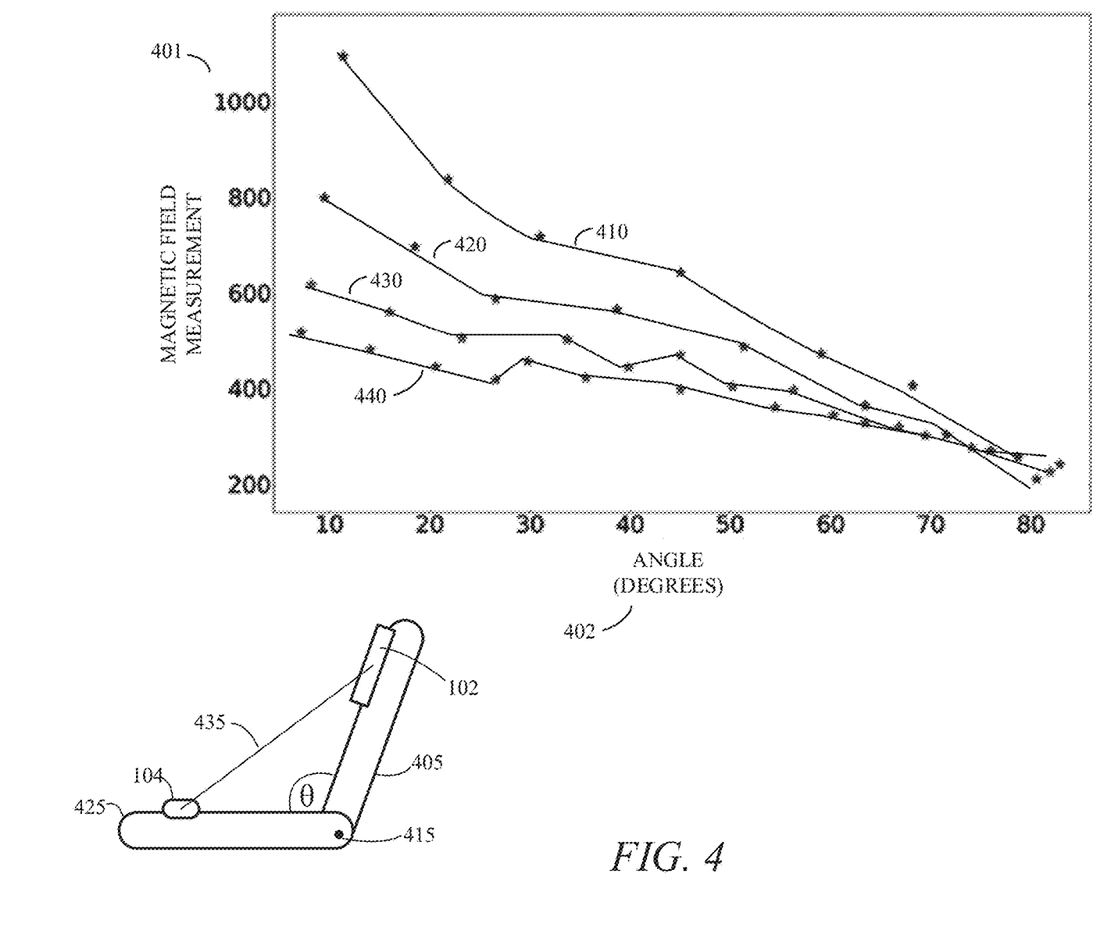
FIG. 4 illustrates an example of biomechanical measurement device characteristics for various sensor distances in accordance with implementations of the present disclosure.

FIG. 4 illustrates an example of biomechanical measurement device characteristics for various relative sensor distances in accordance with implementations of the present disclosure. In some implementations, characteristic curves 410/420/430/440 for a biomechanical measurement device, such as apparatus 100 of FIG. 1, may be generated based on correspondence between magnetic field intensity measurements 401 with respect to measured angle 402. For example, magnet 102 may be attached to a body segment 405 and magnetic sensor 104 may be attached to body segment 425, having a relative distance 435 between them with respect to a body segment joint 415. The biomechanical measurement characteristic curves 410/420/430/440 may be generated by performing a series of measurements of between the magnet 102 and the magnetic sensor 104 at different relative distances 435 between the magnet 102 and the magnetic sensor 104. For example, the wearable magnet 102 may be placed on body segment 405 at a first relative distance 435, and by measuring at varying relative angles θ, correspondence curve 410 may be generated. Similarly, another correspondence curve 420/430/440 may be generated for correspondence of measured magnetic field intensity 401 to angle 402 for a different relative distance 435. For example, correspondence curves 410/420/430/440 can be based on relative distances of 12 in./9 in./6 in./3 in., respectively, which is indicative of a greater variance of magnetic field intensity range at greater relative distances.

The biomechanical measurement characteristic curves 410/420/430/440 may be stored in memory unit 108 for reference by the microcontroller 106 when generating biomechanical motion outputs by mapping received measurements of magnetic field intensity 401 to a corresponding angle 402 for a respective relative distance 435.

Figure 5:
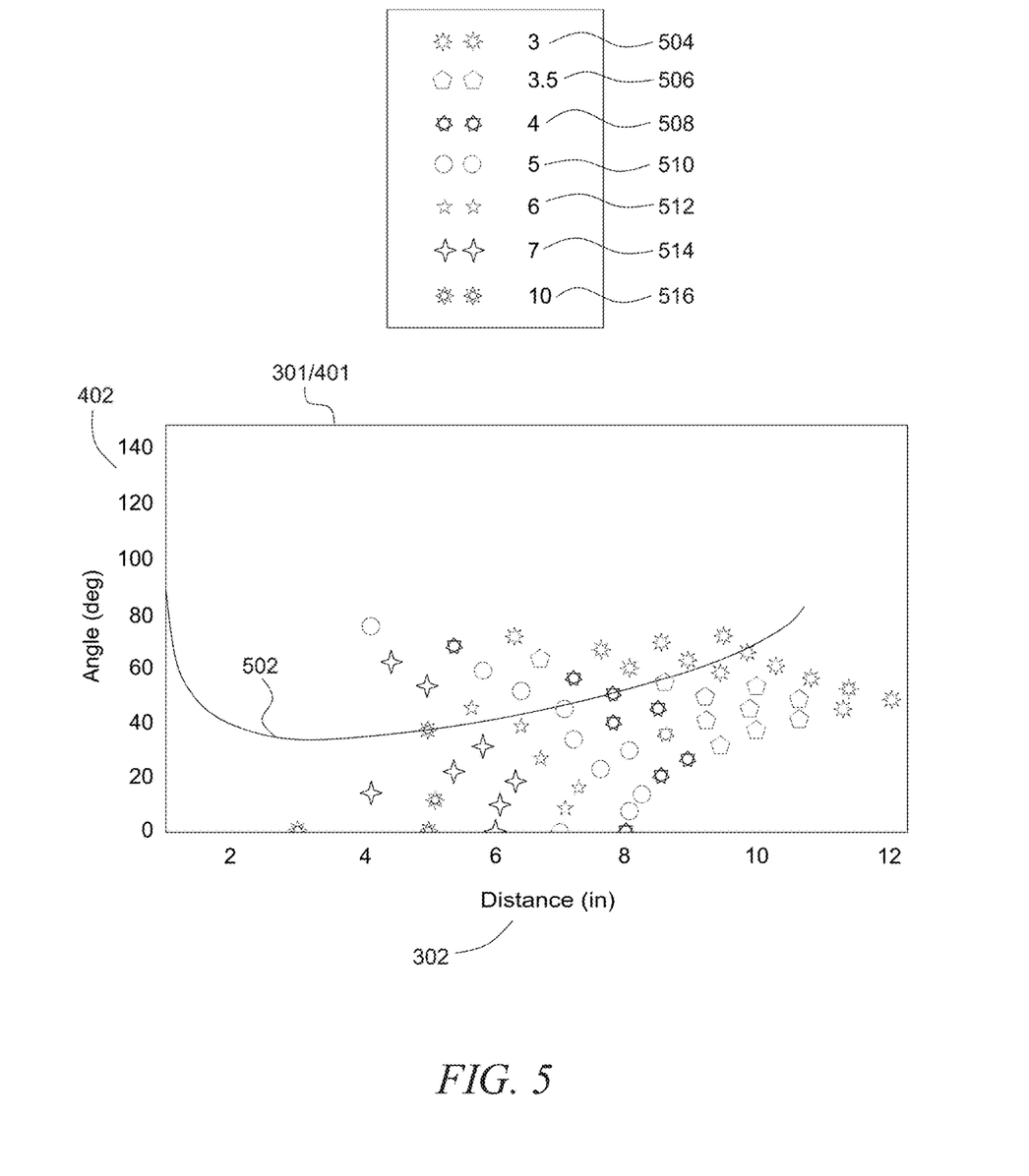
FIG. 5 illustrates an example of biomechanical measurement device characteristics for various sensor orientations and various sensor distances in accordance with implementations of the present disclosure.

FIG. 5 illustrates an example of biomechanical measurement device characteristics for various sensor orientations and various sensor distances in accordance with implementations of the present disclosure. In some implementations, characteristics (e.g., in form of line or scatterplot groups) 504-516 for a biomechanical measurement device, such as apparatus 100 of FIG. 1, may be generated based on correspondence between magnetic field intensity measurements 301/401, relative distances 302, and measured angle 402. Each of scatterplot groups 504-516, for example, can represent various combinations of relative distance 302 and measured angle 402 that yield a certain magnetic field intensity. For example, various combinations of the relative distance 302 and measured angle 402 yield the same magnetic field intensity. The biomechanical measurement characteristics 504-516 can be generated by performing a series of measurements between the magnet 102 and the magnetic sensor 104 at different relative orientation angles θ between the magnet 102 and the magnetic sensor 104, and at different relative distances 435 between the magnet 102 and the magnetic sensor 104. For example, the wearable magnet 102 may be placed on body segment 405 at a first relative orientation angle θ and at a first relative distance 435, and by measuring at varying relative angles θ and relative distances 435 to make the measured magnetic field intensity constant (e.g., an intensity of 3), the correspondence scatterplot group 504 may be generated. Similarly, other correspondence scatterplot groups 506-516 may be generated for correspondence of measured magnetic field intensity 301/401 to distance 302 and angle 402.

As can be seen from FIG. 5, the actual combination of relative distance 302 and relative angle 402 cannot be uniquely determined based on only one signal intensity (e.g., an intensity value of 5). For example, a magnetic field intensity of 5, which corresponds to scatterplot group 510, can represent a combination of a relative distance of 6 inches and a relative angle of 60 degrees, or another combination of a relative distance of 8 inches and a relative angle of 10 degrees. However, if relative distance 302 and relative angle 402 change (e.g., in a scenario of one body-segment move), the magnetic field intensity 301/401 can change accordingly. In some implementations, a biomechanical model can be used to assist determination of the actual combination of relative distance 302 and relative angle 402. For example, the biomechanical model can take into account anatomy of human bodies, magnet properties, and sensor magnet positions, based on which only certain combinations of relative distance 302 and relative angle 402 are possible. For example, in FIG. 5, a biomechanical model can be represented by a biomechanical model curve 502. In the example with a magnetic field intensity of 5 corresponding to scatterplot group 510, for example, biomechanical model curve 502 passes through a point representing a combination of a relative distance of 7 inches and a relative angle of 50 degrees, which is the unique combination under the constraint of the biomechanical model. The biomechanical model can take various forms, such as, for example, curves, plots, functions, graphs, spreadsheets, statistical models, etc.

Going back to FIG. 4, in some implementations, a relative distance between the magnet 102 and the sensor 104 may be selected from a set of candidate relative distances depending on the type of biomechanical motion to be measured. As set forth in the foregoing description, based on the measured magnetic field intensity 401 as a function of relative distance 302 and relative angle 402, permissible ranges of relative distance 302 and relative angle 402 limited by placement of magnet 102 and magnetic sensor 104 on the body, and the biomechanical model that constrains permissible changes of the magnetic field intensity 401, a curve of 410/420/430/440 can be selected. For example, measurement of spinal motion may include selection of a relative distance 435 based on an expected placement of magnet 102 and magnetic sensor 104. As another example, for measurement of ankle motion, a relative distance 435 may be selected based on a tighter relative distance based on the ankle region's physical geometry being smaller than that of the spinal region. A computing device, such as the microcontroller 106 of FIG. 1, may select a characteristic curve 410/420/430/440 in response to a user input using user interface 110 during the initial setup of the measurement apparatus 100. For example, user interface 110 may present selectable options as a display, such as according to the body segment to be measured, or according to the approximate relative distances of the magnet 102, sensor 104, body segment joint 315, or a combination thereof. From the displayed options, user interface 110 may respond to user input, such as, for example, by touchscreen input selections. The characteristic curve can be preselected, such as by the computing device or the user. In some implementations, a characteristic curve 410/420/430/440 can be selected in response to a calibration process initiated or executed by the user or the apparatus 100. For example, in the calibration process, the user can put the magnet and magnetic sensor on different body parts, then move the different body parts within the possible ranges of relative distance and relative angle for a few times, during which movement the magnetic sensor can measure and track the magnetic field intensity at the endpoints of characteristic curves 410-440. The possible ranges of relative distance and relative angle can include, for example, some or all possible ranges associated with the body mechanics. Based on the measured and tracked magnetic field intensity at the endpoints, a characteristic curve can be selected.

Figure 6:
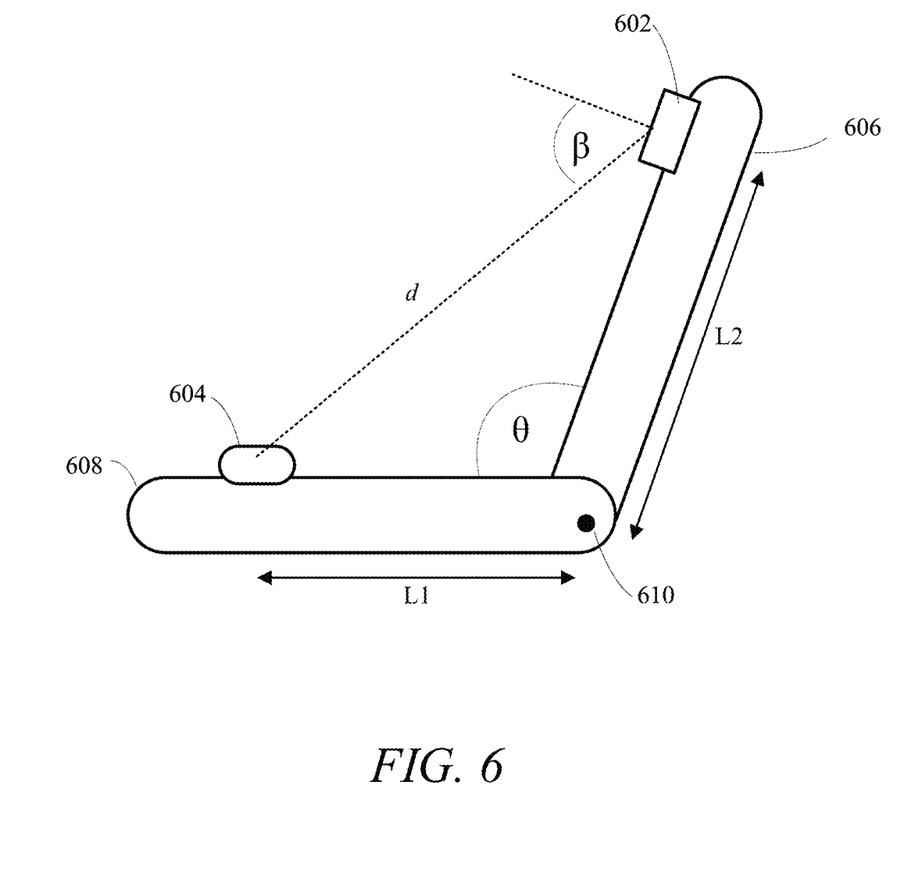
FIG. 6 is a diagram of planar biomechanical metrics in accordance with implementations of the present disclosure.

FIG. 6 is a diagram of planar biomechanical metrics in accordance with implementations of the present disclosure. In some implementations, a wearable magnet 602 may be placed on a first body segment 606, and a wearable magnetic sensor 604 may be placed on a second body segment 608. Relative metrics may include a relative angle θ between body segments 606/608 and a relative distance d between magnet 602 and sensor 604. Distance L1 between body segment joint 610 and sensor 604 and distance L2 between body segment joint 610 and magnet 602 may be predetermined by physical coupling between the magnet 602 and the sensor 604, or by instructing the user to comply with predetermined distances L1, L2 when placing the magnet 602 and the sensor 604 onto body segments 606/608. In some implementations, distances L1, L2 can be determined in response to a calibration process by the user, an example of which is described above with reference to FIG. 5. For example, in FIG. 6, during the calibration process, a certain number of movements associated with the first body segment 606 and the second body segment 608 can be performed by the user, ranging from various relative distances d and various relative angles θ. Based on a biomechanical model (e.g., the biomechanical model curve 502 shown in FIG. 5), which can be selected from multiple biomechanical models based on either or the combination of the first body segment 606 and the second body segment 608, the actual combination of (d, θ) for each of the movements can be determined. Based on the determined combination of (d, θ) for a given movement, parameters such as some or all of d, θ, L1, L2 can be established using, for example, trigonometry (e.g., the law of cosines), from which the values of L1, L2 can be solved.

A measured magnetic field intensity I may be proportional to the inverse cube of the relative distance d between the magnet and the magnetic sensor, according to the following equation:

$$I=(c/d^3)f(\beta)$$ Equation (1)

where c is a constant defined by magnet strength, and $f(\beta)$ represents the change in magnetic field intensity as a function of angle β for non-isotropic magnets. For example, angle β may be relative to north-south poles. For isotropic magnets, the relative distance d may be determined from the signal intensity more directly based on an inverse square relationship.

In some implementations, the biomechanical model may provide characteristics of the magnetic field intensities with respect to relative distances d and angles β, θ. The relationship of angles β, θ can be determined based on an expected orientation of magnetic poles for the magnet as attached to the body segment. Using the biomechanical model for a configuration of the magnet and the magnetic sensor, several input intensity I measurements can be processed, and the change in magnetic field intensity I can be computed. The relative distance d may then be derived according to Equation (1).

Figure 7:
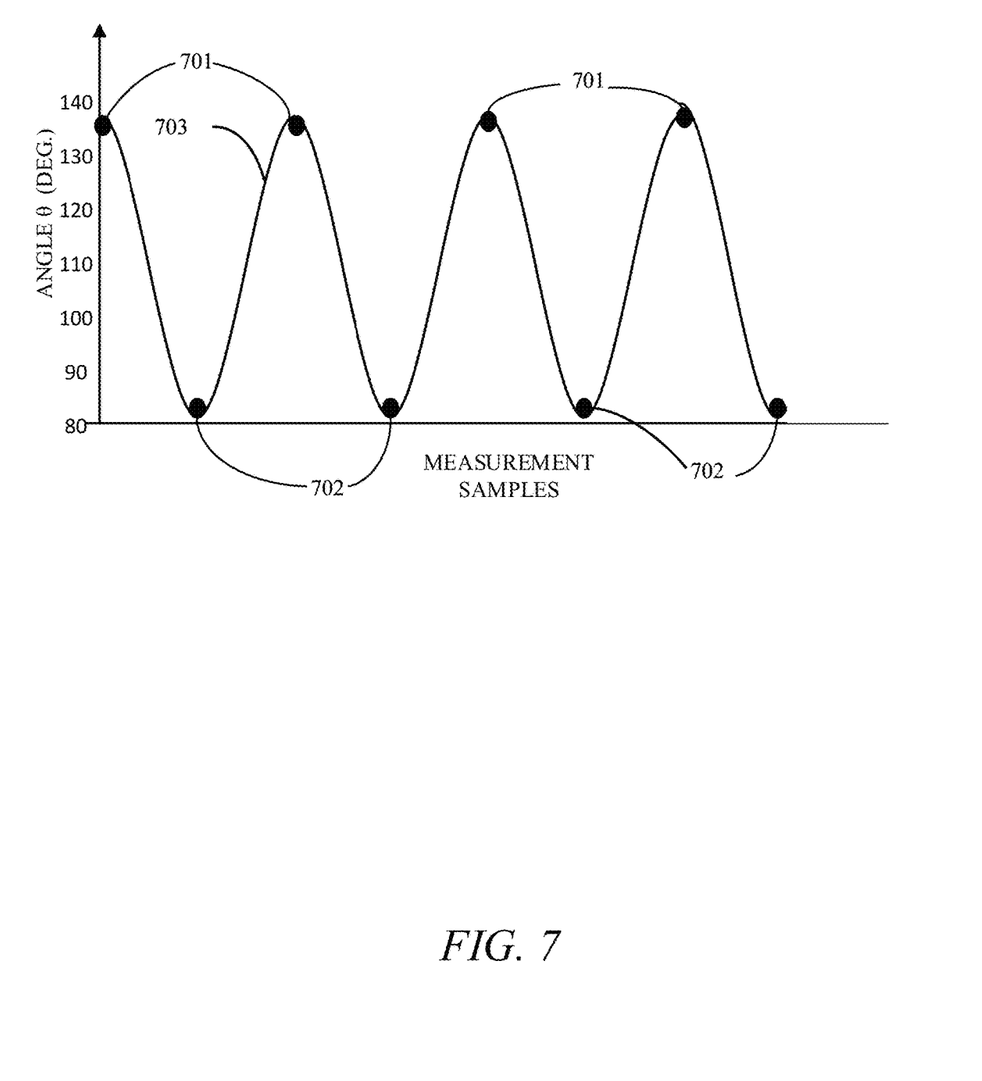
FIG. 7 illustrates an example of a biomechanical model for relative orientation angle in accordance with implementations of the present disclosure.

FIG. 7 illustrates an example of a biomechanical model for relative orientation angle in accordance with implementations of the present disclosure. In some implementations, a two-dimensional biomechanical model may be generated according to a function of relative distance d between the magnetic sensor 104 and the magnet 102 and the relative angle θ, which may have the following relationship constraint:

$$d=\sqrt{L_1^2+L_2^2-2L_1L_2\cos(\theta)}$$ Equation (2)

As shown in FIG. 7, various measurements 701/702 may be taken at extreme relative angles θ. A biomechanical model for relative angle θ may be generated as estimation curve 703, derived from the function of Equation (2) based on the measurements 701/702, distances L1, L2, and relative distance d. For example, a measurement of ankle motion may be determined by the placement of the wearable magnet 102 on a shoe and the wearable magnetic sensor 104 on the lower leg of a user, and measurements 701 may be taken during a full plantarflexion of the ankle as a first limiting relative angle θ, and measurements 702 may be taken during a full dorsiflexion of the ankle as a second limiting relative angle θ. In some implementations, once the biomechanical model is generated, such as according to the estimation curve 703, measurements by the wearable magnetic sensor 104 may be translated and mapped to the curve of function 703, such that a corresponding angle θ for the body segment motion can be determined.

Figure 8:
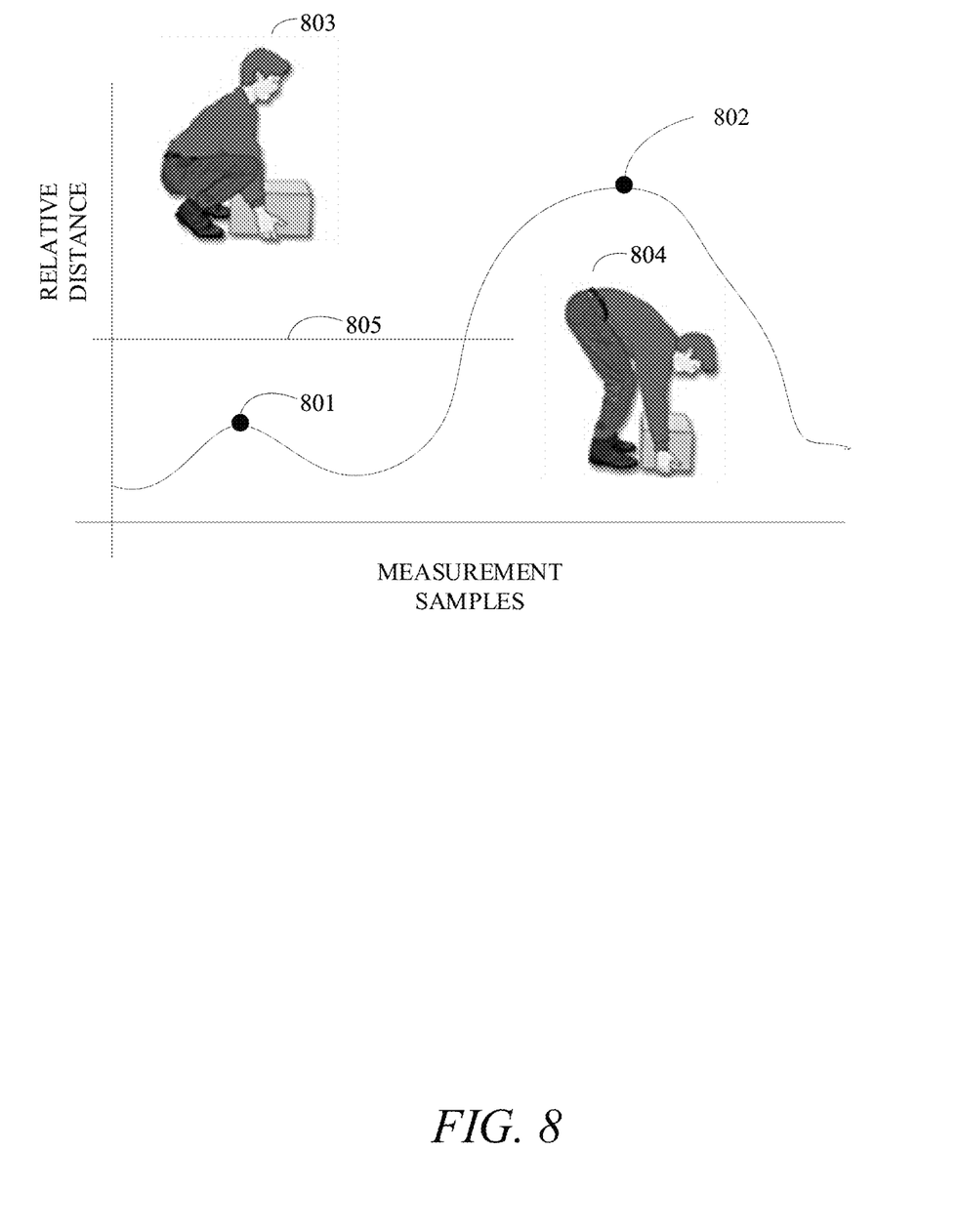
FIG. 8 illustrates an example of biomechanical motion measurement in accordance with implementations of the present disclosure.

FIG. 8 illustrates an example of biomechanical motion measurements in accordance with implementations of the present disclosure. In some implementations, a biomechanical model may be generated based on the relative distance between a wearable magnet 102 and a wearable magnetic sensor 104. For example, a threshold 805 may be determined based on a measurement 801 performed during proper body segment motion 803 and a measurement 802 performed during improper body segment motion 804. During monitoring of spinal motion, biomechanical output may be generated indicating that the threshold 805 has been exceeded, and a feedback signal, such as a visual or audio notification at user interface 110, may be generated in response to the detected threshold.

Examples of body segment motion measurement according to the disclosure herein may, without limitation, include the following: In an aspect, ankle movement may be measured by placement of the magnet 102 on the lower leg and the magnetic sensor 104 on a shoe of the user. In another aspect, to track proper lifting technique and/or address lower back pain, spinal motion may be measured by placement of the magnet 102 on the pelvis or waist, and placement of the magnetic sensor 104 on the spinal region. In another aspect, scapula protraction may be monitored and measured by placement of the magnet 102 on the scapula region and the sensor 104 on the spinal region.

In some implementations, frequency-based metrics may be determined. For example, respiratory rate may be monitored by placement of the magnet 102 on the chest region, and placement of one or more magnetic sensors 104 on an adjacent arm region. Such an arrangement may allow detection of the user's respiratory rate while the user is moving about, and may also allow measurement of other physiological signals or movements with the same sensors. In some implementations, a low-pass filter may be applied to remove higher frequency content. Optional adaptive filters based on accelerometer reference input may be used to remove or reduce motion artifacts. Periods between oscillations in time domain can be calculated, or fundamental frequency in frequency domain can be selected.

In some implementations, multiple magnetic sensors can be used in conjunction with the magnet. For example, the one magnet and the two magnetic sensors can be placed on different body segments. Another example can be one sensor and a smartphone equipped with a magnetometer. In an aspect, enhanced gesture control can be developed to share the magnet between the sensor and the smartphone. Relative changes in the distances between the magnet and the multiple devices can be used to detect gestures, even without any direct communication between the sensor and the smartphone. For example, the pair of relative distances may be represented by a triangulation function, which may determine a more accurate gesture control than can be achieved by a single motion sensor used in conventional user devices.

In an aspect, a magnetic sensor may be placed in a shoe of the user, a magnet may be placed on the user's lower leg, and a smartphone may be placed in a pocket in the user's thigh region. By applying multiple sensors, multibody biomechanical analysis may be performed by measuring metrics for running and gait analysis more accurately.

The embodiments herein may be described in terms of functional block components and various processing steps. The disclosed processes and sequences may be performed alone or in any combination. Functional blocks may be realized by any number of hardware and/or software components that can perform the specified functions. For example, the described embodiments may employ various integrated circuit components, such as memory elements, processing elements, logic elements, look-up tables, and the like, which may carry out a variety of functions under the control of one or more microprocessors or other control devices. Similarly, where the elements of the described embodiments are implemented using software programming or software elements, the present disclosure may be implemented with any programming or scripting language such as C, C++, Java, assembler, or the like, with the various algorithms being implemented with any combination of data structures, objects, processes, routines, or other programming elements. Functional aspects may be implemented in algorithms that execute on one or more processors. Furthermore, the embodiments of the present disclosure could employ any number of conventional techniques for electronics configuration, signal processing and/or control, data processing, and the like.

Aspects or portions of aspects of the above disclosure can take the form of a computer program product accessible from, for example, a computer-usable or computer-readable medium. A computer-usable or computer-readable medium can be any device that can, for example, tangibly contain, store, communicate, or transport a program or data structure for use by or in connection with any processor. The medium can be, for example, an electronic, magnetic, optical, electromagnetic, or semiconductor device. Other suitable mediums are also available. Such computer-usable or computer-readable media can be referred to as non-transitory memory or media, and may include RAM or other volatile memory or storage devices that may change over time. A memory of an apparatus described herein, unless otherwise specified, does not have to be physically contained by the apparatus, but is one that can be accessed remotely by the apparatus, and does not have to be contiguous with other memory that might be physically contained by the apparatus.

The word "example" is used herein to mean serving as an example, instance, or illustration. Any aspect or design described herein as an "example" is not necessarily to be construed as being preferred or advantageous over other aspects or designs. Rather, use of the word "example" is intended to present concepts in a concrete fashion. As used in this application, the term "or" is intended to mean an inclusive "or" rather than an exclusive "or." That is, unless specified otherwise, or the context clearly suggests otherwise, the statement "X includes A or B" is intended to mean any of the natural inclusive permutations thereof. In other words, if X includes A, X includes B, or X includes both A and B, then "X includes A or B" is satisfied under any of the foregoing instances. In addition, unless specified otherwise or the context clearly suggests that they are to be directed to a singular form, the articles "a" and "an" as used in this application and the appended claims should generally be construed to mean "one or more". Moreover, use of the term "an aspect" or "one aspect" throughout this application is not intended to mean the same embodiment or aspect unless described as such.

The particular aspects shown and described herein are illustrative examples of the present disclosure and are not intended to otherwise limit the scope of the present disclosure in any way. For the sake of brevity, conventional electronics, control systems, software development, and other functional aspects of the systems, methods, and apparatuses described herein (and components of the individual operating components of the systems, methods, and apparatuses described herein) may not be described in detail herein. Furthermore, the connecting lines, or connectors, shown in the various figures presented are intended to represent examples of functional relationships and/or physical or logical couplings between the various elements. Many alternative or additional functional relationships, physical connections, or logical connections may be present in a practical device.

The use of "including" or "having" and variations thereof herein is meant to encompass the items listed thereafter and equivalents thereof as well as additional items. Unless specified or limited otherwise, the terms "mounted," "connected," "supported," "coupled," and variations thereof are used broadly and encompass both direct and indirect mountings, connections, supports, and couplings. Further, "connected" and "coupled" are not restricted to physical or mechanical connections or couplings.

The use of the terms "a," "an," "the," and similar referents in the context of describing the present disclosure (especially in the context of the following claims) should be construed to cover both the singular and the plural. Furthermore, recitation of ranges of values herein are intended merely to serve as a shorthand method of referring individually to each separate value falling within the range, unless otherwise indicated herein, and each separate value is incorporated into the specification as if it were individually recited herein. Finally, the steps of all methods described herein are performable in any suitable order unless otherwise indicated herein or otherwise clearly contradicted by the context. The use of any and all examples, or language provided herein suggesting that an example is being made (e.g., "such as"), is intended merely to better illuminate the present disclosure and does not impose a limitation on the scope of the present disclosure unless otherwise claimed.

The above-described embodiments have been described in order to facilitate easy understanding of the present disclosure and do not limit the present disclosure. To the contrary, the present disclosure is intended to cover various modifications and equivalent arrangements included within the scope of the appended claims, which scope is to be accorded the broadest possible interpretation so as to encompass all such modifications and equivalent arrangements as is permitted under the law.

What is claimed is:

1. A method for measuring relative body movement with a wearable device, comprising:
receiving, from a magnetic sensor of the wearable device, first signal data indicative of a magnetic field of a wearable magnet, wherein the wearable device is placed on a first body segment and the wearable magnet is placed on a second body segment;
determining, by a computing device based on the first signal data, a distance metric indicative of a relative distance between the wearable magnet and the wearable device, and an orientation metric indicative of an orientation of the magnet sensor relative to the wearable magnet; and
determining a biomechanical model based on a type of body segment for the first body segment and the second body segment, wherein the biomechanical model includes a relationship constraint between the distance metric and the orientation metric, wherein the relationship constraint is a planar function to determine, for a joint junction of the first body segment and the second body segment, a relative angle indicative of a relative angular movement between the first body segment and the second body segment based on the orientation of the wearable magnet, and the relative angle is determined based on a first length between the joint junction and the wearable magnet and a second length between the junction joint and the wearable device.

2. The method of claim 1, further comprising:
generating biomechanical output data indicative of a relative posture for the first body segment and the second body segment based on the biomechanical model.

3. The method of claim 2, further comprising:
sending a feedback signal in response to a detection of the distance metric or the orientation metric exceeding a threshold.

4. The method of claim 1, wherein the first signal data includes a measurement of magnetic field intensity of the wearable magnet as detected by the wearable device.

5. The method of claim 4, wherein on a condition that the wearable magnet is isotropic, the distance metric is determined as a function of measured magnetic field intensity proportional to an inverse cube of distance between the wearable magnet and the wearable device.

6. The method of claim 4, wherein on a condition that the wearable magnet is anisotropic, the distance metric is determined as a function of measured magnetic field intensity proportional to an inverse cube of distance between the wearable magnet and the wearable device,
wherein the measured magnetic field intensity is based on a function of a magnetic field intensity change relative to an angular displacement between the wearable device and the wearable magnet.

7. The method of claim 6, further comprising:
mapping the measured magnetic field intensity relative to the distance metric for various wearable magnet orientations over iterative measurements; and
revising the biomechanical model based on the mapping.

8. The method of claim 1, wherein the relative angle for the joint junction of the first body segment and the second body segment is determined based on the orientation of the wearable magnet normal to the second body segment.

9. The method of claim 1, wherein the relationship constraint is a function of the law of cosines.

10. An apparatus, comprising:
a wearable magnet removably attachable to an accessory component configured to be attached to a first body segment; and
a wearable device configured to be attached to a second body segment, comprising:
a magnetic sensor for detecting a magnetic field intensity of the wearable magnet, and
a computing device configured to:
receive, from the magnetic sensor, first signal data indicative of a magnetic field of a wearable magnet;
determine a distance metric indicative of a relative distance between the wearable magnet and the wearable device, and an orientation metric indicative of an orientation between the wearable magnet and the magnetic sensor; and
determine a biomechanical model based on a type of body segment for the first body segment and the second body segment, wherein the biomechanical model includes a relationship constraint between the distance metric and the orientation metric, wherein the relationship constraint is a planar function to determine, for a joint junction of the first body segment and the second body segment, a relative angle indicative of a relative angular movement between the first body segment and the second body segment based on the orientation of the wearable magnet, and the relative angle is determined based on a first length between the joint junction and the wearable magnet and a second length between the junction joint and the wearable device.

11. The apparatus of claim 10, wherein the computing device is further configured to generate feedback data indicative of a relative posture for the first body segment and the second body segment based on the biomechanical model.

12. The apparatus of claim 11, wherein the computing device is further configured to generate feedback data in response to a detection of the distance metric or the orientation metric exceeding a threshold.

13. The apparatus of claim 10, wherein the wearable magnet is isotropic, and the computing device is further configured to determine the distance metric as a function of the measured magnetic field intensity proportional to an inverse cube of a distance between the wearable magnet and the wearable device.

14. The apparatus of claim 10, wherein the wearable magnet is anisotropic, and the computing device is further configured to determine the distance metric as a function of the measured magnetic field intensity proportional to an inverse cube of distance between the wearable magnet and the wearable device,
wherein the measured magnetic field intensity is based on a function of a magnetic field intensity change relative to angular displacement between the wearable device and the wearable magnet.

15. The apparatus of claim 10, wherein the computing device is further configured to measure respiratory rate on a condition that the wearable magnet is placed on a chest region, and the wearable device is placed on an arm region.

16. The apparatus of claim 10, wherein the computing device is further configured to measure scapular posture on a condition that the wearable magnet is placed on a scapular region, and the wearable device is placed on a spinal region.

17. The apparatus of claim 10, wherein the computing device is further configured to measure lower back posture on a condition that the wearable magnet is placed on a pelvic region, and the wearable device is placed on a spinal region.

18. The apparatus of claim 10, wherein the computing device is further configured to measure ankle posture on a condition that the wearable magnet is placed on a lower leg region, and the wearable device is placed on a foot region.

19. An apparatus, comprising:
a wearable magnet removably attachable to an accessory component configured to be attached to a first body segment;
a wearable device configured to be attached to a second body segment, comprising a first magnetic sensor for detecting a first magnetic field intensity of the wearable magnet; and
a computing device configured to be attached to a third body segment, comprising a second magnetic sensor for detecting a second magnetic field intensity of the wearable magnet, the computing device configured to:
receive, from the first magnetic sensor, first signal data indicative of a magnetic field of a wearable magnet;

determine a distance metric indicative of a first relative distance between the wearable magnet and the first magnetic sensor and a second relative distance between the wearable magnet and the second magnetic sensor, and an orientation metric indicative of an orientation between the wearable magnet and the magnetic sensor;

determine a biomechanical model based on the type of body segment for the first body segment, the second body segment, and the third body segment, wherein the biomechanical model includes a relationship constraint between the distance metric and the orientation metric, wherein the relationship constraint is a planar function to determine, for a joint junction of the first body segment and the second body segment, a relative angle indicative of a relative angular movement between the first body segment and the second body segment based on the orientation of the wearable magnet, and the relative angle is determined based on a first length between the joint junction and the wearable magnet and a second length between the junction joint and the wearable device; and generate biomechanical output data indicative of a relative posture for the first body segment, the second body segment, and the third body segment based on the biomechanical model.

* * * * *